(12) United States Patent
Guiraud (10) Patent No.: US 11,690,816 B2
(45) Date of Patent: Jul. 4, 2023

(54) UNIT DOSES FOR IMMEDIATE RELEASE OF GHB OR OF ONE OF THE THERAPEUTICALLY ACCEPTABLE SALTS THEREOF, ADMINISTERED ORALLY, AND THE USE THEREOF TO MAINTAIN ALCOHOL ABSTINENCE

(71) Applicant: DEBREGEAS ET ASSOCIES PHARMA, Paris (FR)

(72) Inventor: Julien Guiraud, Clichy la Garenne (FR)

(73) Assignee: DEBREGEAS ET ASSOCIES PHARMA, Paris (FR)

( * ) Notice: Subject to any disclaimer, the term of this patent is extended or adjusted under 35 U.S.C. 154(b) by 571 days.

(21) Appl. No.: 16/084,075

(22) PCT Filed: Mar. 30, 2017

(86) PCT No.: PCT/FR2017/000060
§ 371 (c)(1),
(2) Date: Sep. 11, 2018

(87) PCT Pub. No.: WO2017/168059
PCT Pub. Date: Oct. 5, 2017

(65) Prior Publication Data
US 2019/0255001 A1    Aug. 22, 2019

(30) Foreign Application Priority Data
Apr. 1, 2016 (FR) .................... 16/00554

(51) Int. Cl.
*A61K 31/19* (2006.01)
*A61P 25/32* (2006.01)
*A61K 9/50* (2006.01)

(52) U.S. Cl.
CPC ............ *A61K 31/19* (2013.01); *A61K 9/5073* (2013.01); *A61K 9/5078* (2013.01); *A61P 25/32* (2018.01)

(58) Field of Classification Search
CPC .. A61K 31/519; A61K 31/337; A61K 31/437; A61K 31/439; A61K 31/513;
(Continued)

(56) References Cited

U.S. PATENT DOCUMENTS 8,591,922 B1    11/2013    Allphin et al.
2009/0137565 A1    5/2009    Frucht
(Continued)

FOREIGN PATENT DOCUMENTS

EP    1 017 381 B1    2/2005
WO    2006/053186 A2    5/2006
(Continued)

OTHER PUBLICATIONS

Addolorato, An Open Multicentric Study Evaluating 4-Hydroxybutyric Acid Sodium Salt in the Medium-Term Treatment of 179 Alcohol Dependent Subjects, Alcohol & Alcoholism, 1996, 31(4), pp. 3413-3445 (Year: 1996).*
(Continued)

*Primary Examiner* — Savitha M Rao
*Assistant Examiner* — Andrew P Lee
(74) *Attorney, Agent, or Firm* — Oliff PLC (57) ABSTRACT

An immediate release, unit doses of GHB or one of the therapeutically acceptable salts thereof administered via oral route. Such unit doses contain between 0.37 and 1.75 g of GHB, when under the form of granules, these granules have the following composition (weight % relative to the total weight of the granule):
Active ingredient (sodium oxybate): 50 to 60%;
Effervescent agent: 5 to 15%;
(Continued)

Diluent: 2 to 18%;
Binder: 3 to 10%;
Substrate (Solid core of the granule): 15 to 25%;
Coating agent/flavouring agent/sweetening agent/lubricant: 3 to 6%.

Application for maintaining abstinence from alcohol of patients with mild or moderate alcohol dependence or with severe or very severe alcohol dependence, either suffering or not from liver disease.

11 Claims, 6 Drawing Sheets

(58) Field of Classification Search
CPC .............. A61K 31/5377; A61K 31/553; A61K 31/7068; A61K 33/243; A61K 45/06; A61K 31/7072; A61K 39/39558; A61K 33/24; A61K 45/00; A61P 35/00; A61P 43/00; C07D 487/04
See application file for complete search history.

(56) References Cited

U.S. PATENT DOCUMENTS

| | | |
|---|---|---|
| 2010/0112056 A1 | 5/2010 | Rourke et al. |
| 2012/0076865 A1 | 3/2012 | Allphin et al. |
| 2014/0348917 A1 | 11/2014 | Rourke et al. |

FOREIGN PATENT DOCUMENTS

| | | | | |
|---|---|---|---|---|
| WO | 2010/053691 A1 | 5/2010 | | |
| WO | 2011/119839 A1 | 9/2011 | | |
| WO | 2011/139271 A1 | 11/2011 | | |
| WO | WO-2011139271 A1 * | 11/2011 | ........... | A61K 9/2072 |
| WO | 2012/107652 A1 | 8/2012 | | |

OTHER PUBLICATIONS

Pardi, Daniel et al. "γ-Hydroxybutyrate/Sodium Oxybate Neurobiology, and Impact on Sleep and Wakefulness". CNS Drugs, vol. 20, p. 887-912, 2006.
Ferrara, S.D. et al. "Effect of moderate or severe liver dysfunction on the pharmacokinetics of γ-hydroxybutyric acid". Pharmacokinetics and Disposition, p. 305-310, 1996.
"Sevrage simple en alcool". Société Française d'Alcoologie, p. 1-4, 2006.
Skala, Katrin et al. "Sodium oxybate in the treatment of alcohol dependence: from the alcohol withdrawal syndrome to the alcohol relapse prevention". Expert Opinion, vol. 15, p. 245-257, 2014.
Addolorato, Giovanni et al."The therapeutic potential of gamma-hydroxybutyric acid for alcohol dependence: balancing the risks and benefits. A focus on clinical data". Expert Opinion, vol. 18, p. 675-686, 2009.
Jun. 2, 2017 International Search Report issued in International Patent Application No. PCT/FR2017/000060.

* cited by examiner

UNIT DOSES FOR IMMEDIATE RELEASE OF GHB OR OF ONE OF THE THERAPEUTICALLY ACCEPTABLE SALTS THEREOF, ADMINISTERED ORALLY, AND THE USE THEREOF TO MAINTAIN ALCOHOL ABSTINENCE

The present invention concerns immediate release, unit doses of GHB or one of the therapeutically acceptable salts thereof administered via oral route, and the use thereof for maintaining abstinence from alcohol.

Sodium oxybate, which is the most widely used salt of hydroxybutyric acid (GHB), is employed for therapeutic purposes in the treatment of the following pathologies:
  alcohol dependence: treatment of alcohol withdrawal syndrome and maintaining of alcohol abstinence in alcohol-dependent patients;
  narcolepsy in patients suffering from cataplexy,
  anaesthesia.

It is listed by the 1971 convention on psychotropic substances.

For therapeutic use, it is important that the optimal dosage of sodium oxybate should be well determined to enhance the benefit-risk ratio and to avoid any risk of over- or under-dosage.

The treatment of alcohol dependence takes place in two phases.

During the first phase, the patients are weaned and optionally treated in the event of severe withdrawal syndrome. Alcohol withdrawal syndrome is commonly used to describe the group of symptoms which occur on gradual or sudden stopping of alcohol intake by alcohol-dependent patients. These symptoms translate as mental, behavioural and physical side effects. In the majority of cases the syndrome resolves spontaneously or under two- to five-day treatment but mortality is not zero (Société Française d'Alcoologie, 2006). It is treated with anticonvulsants, antipsychotics or with sodium oxybate.

After weaning, a maintained abstinence phase is necessary to improve the patient's state of health and avoid the onset of pathologies related to alcoholism. Abstinence appears to be the only efficient method to halt or reduce the psychological disorders of alcoholism. It is also the only means to reduce impacts on physical health since it has been shown in numerous publications that the risks of alcohol-related morbidity and mortality occurrence are a function of the level of the daily consumption of alcohol.

Treatment of maintained abstinence is composed of psychosocial follow-up and pharmacological treatments over periods of several months.

In Italy and Austria, sodium oxybate has been indicated and used in the treatment of alcohol withdrawal and maintaining of abstinence for more than 20 years and 15 years respectively. Its efficacy in these indications and its safe use have been researched in numerous published clinical trials and the treatment has been given to several hundred thousand patients.

An article signed Giovanni Addolorato, Lorenzo Leggio, Anna Ferrulli, Fabio Caputo and Antonio Gasbarrini (Expert Opinion on Investigational Drugs. 2009; 18 (5): 675-686) confirms the advantage of GHB in the treatment of alcohol-dependent patients. In this article, the effective doses vary from 50 to 100 mg/kg per day (divided over three administrations) as a function of the indication, namely alcohol withdrawal or maintaining of abstinence.

Patent application WO 2011/119839 describes a controlled release pharmaceutical composition, and not immediate release, whereas this latter type of release is essential in the treatment of alcohol abstinence. In addition, this application refers to the use of GHB for the treatment of narcolepsy and fibromyalgia, that are far removed from a treatment intended for the maintaining of alcohol abstinence.

Patent application WO 2011/139271 describes an immediate release pharmaceutical composition, but it concerns the treatment of narcolepsy.

American patent application US 2010/112056 also describes an immediate release pharmaceutical composition, but it concerns the treatment of narcolepsy, fibromyalgia and sleeping disorders.

Patent application WO 2006/053186 describes a pharmaceutical composition intended to treat abnormal movements.

According to a more recent study by K. Skala et al., (Expert Opin. Pharmacoter. 2013; 15 (2)), the recommended dose in the field of maintaining alcohol abstinence is 50 mg/kg divided over three administrations per day.

On the basis of all clinical trials, the Austrian and Italian health authorities authorised the prescribing of sodium oxybate for the maintaining of abstinence with a dosage of 50 mg/kg/d divided into three administrations which may be increased up 100 mg/kg/d.

Regarding narcolepsy, a drug using sodium oxybate as active ingredient and marketed under the name XYREM®, is recommended with a dosage of 4.5 to 9 g per day, taken in two divided doses per night. In addition, various patents describe the use of GHB for the treatment of narcolepsy e.g. international application WO 2010/053691 or patent application US 2014/0348917, both by JAZZ Pharmaceuticals Inc.

Similarly, patent U.S. Pat. No. 8,591,922 (Jazz Pharmaceuticals) describes the use of GHB in the treatment of various sleeping disorders (particularly apnoea, narcolepsy, cataplexy, insomnia, sleep paralysis).

It is to be noted that European patent EP 1017381 (Orphan Medical Inc.) concerns derivatives of butyrate, including sodium oxybate, used in the treatment of fibromyalgia and chronic fatigue syndrome. Nevertheless, since sodium oxybate did not exhibit a positive benefit-risk ratio in the treatment of fibromyalgia and chronic fatigue syndrome, it has no indication for these pathologies and is therefore in theory not used for this purpose.

Irrespective of the indications chosen, it is known that for patients suffering from moderate or severe liver disease, the main pharmacokinetic parameters of GHB or one of the salts thereof are increased by a factor possibly reaching over 120% for one same administered dose, compared with patients not suffering from liver disease (Ferrara et al., 1996). As a result, for these patients it is indicated to divide by one half the dose of GHB, or the salts thereof, as compared with the recommended dosage for patients not suffering from liver disease.

Depending on the dosage and hence the indication under consideration, GHB does not act on the same receptors of the central nervous system on account of a different dosage of active ingredient; this always being calculated as a function of patient weight for the treatment of alcohol dependence.

GHB appears first to act on the GABA-B receptor (gamma-aminobutyric acid) but it directly or indirectly modulates the activity of other neurotransmitters, in particular the dopaminergic, serotoninergic, opioid, cholinergic, noradrenergic, glutamatergic systems (Pardi et al., 2006).

The table below summarises these different parameters as a function of the indication.

|  | Alcohol dependence | Narcolepsy | Anaesthesia |
| --- | --- | --- | --- |
| Dosage | 50 to 100 mg/kg/day | 4.5 to 9 g/day | >10 g |
| Mode of administration | Via oral route 3 times daily | Via oral route X2 times at night | Intravenous injection |
| Receptors/neuro-transmitters predominantly involved at the doses under consideration | Dopaminergics | GABA | GABA |
| Pharmaceutical effects | Stimulant and anxiolytic, able to mimic the effects of alcohol | Restoration of REM sleep quality Sedative | Anaesthetic adjuvant |

It follows from this Table that the effect of GHB ranges from a simple stimulating effect to sedation and anaesthesia as a function of the doses used.

In the present invention, GHB finds application in the treatment of alcohol-related disorders.

More specifically, the application of GHB according to the present invention concerns the maintaining of alcohol abstinence.

For this indication, the prior art always gives GHB dosages expressed in mg/kg, i.e. related to patient weight. These dosages would mean that the optimal dose is a function of patient weight. In addition, the scientific literature does not provide any reason to justify a dose related to patient weight, meaning that the precise choice of dose is essentially empirical, which does not necessarily correspond to the needs of the patient.

Going against this practice, the applicant has found in fully surprising manner that there is no correlation between effective dose and patient weight, and that the problems of alcohol abstinence can be better managed no longer by having recourse to patient weight but to the daily alcohol consumption of the patient, independently of patient weight.

In a recent phase IIb/III clinical trial including 496 patients, four doses of sodium oxybate were compared with a placebo to verify whether the existing dosage (50 mg/kg/d possibly increased up to 100 mg/kg/d) is optimal in terms of efficacy, safety and tolerance. The following doses were examined:

0.75 g sodium oxybate three times daily—i.e. 2.25 g per day (99 patients)
1.25 g sodium oxybate three times daily—i.e. 3.75 g per day (99 patients)
1.75 g sodium oxybate three times daily—i.e. 5.25 g per day (99 patients)
2.25 g sodium oxybate three times daily—i.e. 6.75 g per day (100 patients)
Placebo group (99 patients)

The unit doses, packaged in sachets, were administered via oral route in solid form, more particularly in the form of granules.

Efficacy was measured via percentage days of abstinence (PDA), reduced daily intake of alcohol (TAC) and the number of heavy drinking days (HDD). It was sought to analyse the correlation between efficacy of treatment and dose in mg/kg/d. In this respect the conversion to mg/kg/d was made using the following formula: unit dose in g of sodium oxybate×3/patient weight.

Figure 1:
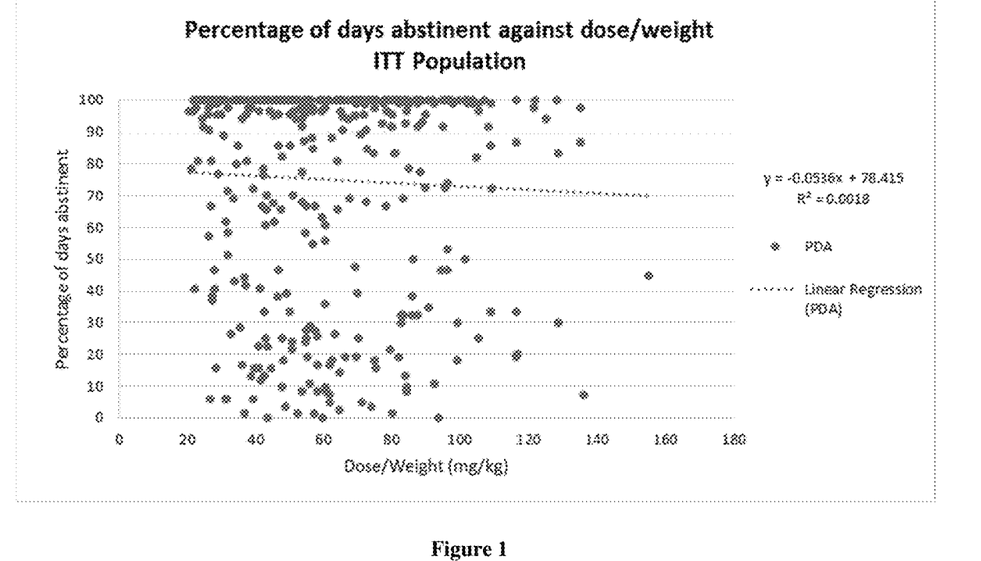

The results for the entire population treated with sodium oxybate (397 patients) are given in FIG. 1 illustrating the efficacy vs. dose relationship in mg/kg.

On the basis of the results illustrated in this Figure, there is no relationship between the efficacy of treatment expressed as a percentage of abstinence days and the dose/weight ratio. The coefficient of correlation $R^2$ is close to 0 (it is very precisely 0.0014) showing that there is no correlation between efficacy and the dose/weight ratio; regarding the slope of the straight line, this can be considered to be zero (it is non-significantly negative).

This observation made on a large number of patients goes against the state of the art.

In the remainder of the present description, reference is made to two categories of alcoholic patients:
patients with mild to moderate alcohol dependence;
patients with severe to very severe alcohol dependence.

These categories are a function of the daily alcohol intake of these different patients as given in the table below:

|  | Daily alcohol intake | |
| --- | --- | --- |
| Patient category | Men | Women |
| Mild alcohol dependence | 1-40 g/day | 1-20 g/day |
| Moderate alcohol dependence | 41-60 g/day | 21-40 g/day |
| Severe alcohol dependence | 61-100 g/day | 41-60 g/day |
| Very severe alcohol dependence | >101 g/day | >61 g/day |

These values correspond to the different risk levels for patient health in relation to daily alcohol intake—low, moderate, high and very high risk—defined by WHO in its document «WHO/MSD/MSB/00.4».

Although varying slightly from one country to another, a standard glass substantially corresponds to 10-12 g of pure alcohol.

With regard to analysis of the results of the phase IIb/III clinical trial given above, the applicant has discovered in fully surprising manner that the optimal dose of sodium oxybate for the maintaining of abstinence is dependent on the level of patient alcohol consumption before weaning.

Low doses (not weight dependent) being the most efficient for patients with low or moderate alcohol dependence, and the higher doses being optimal for patients with severe or very severe alcohol dependence; the optimal doses discovered by the applicant prove to differ significantly from those commonly recommended in the prior art, namely 50 to 100 mg/kg/day in three divided doses. Also, the applicant was able to show that over-dosage or under-dosage in relation to the dosage defined by the applicant could significantly reduce the efficacy of treatment and increase the side effects thereof.

Therefore, application of the dosage determined by the applicant brings an improvement in the efficacy of treatment, prevents over-dosage which may generate undesirable side effects, and simplifies the management of alcohol-dependent patients for whom it is no longer needed to take their weight into consideration to adjust the amount of GHB, or one of the therapeutically acceptable salts thereof, that is to be delivered daily.

The present invention therefore concerns immediate release unit doses containing GHB or one of the therapeutically acceptable salts thereof, such as the sodium salt, to be administered to patients three times daily and in whom it is wished to obtain maintained alcohol abstinence.

In the remainder of the description the term «GHB» covers both gamma-hyroxybutyric acid and the pharmaceutically acceptable salts thereof, and in particular its sodium salt known as sodium oxybate.

The unit dose of GHB is administered via oral route in solid, semi-solid, semi-liquid or liquid form and has immediate release as defined below.

Sodium oxybate is a salt of a weak organic acid, gamma-hydroxybutyric acid having a pKa close to 4.5, and of a strong base sodium hydroxide. It therefore has basic pH and is therefore naturally found in ionic form above a pH of about 4.5. No active systems are known for the transport of sodium oxybate. It is therefore in its non-ionic form at a pH lower than its pKa (4.5) that it can be absorbed by the digestive mucosa. These conditions are only found in the stomach region.

The mean gastric emptying half-time (T50%) under «fasting» conditions i.e. 30 minutes before and 2 hours after meals, is 15 to 20 minutes. It is therefore expected of a pharmaceutical form delivering an active ingredient significantly absorbed solely at the top part of the digestive tract, that it releases this product in a time compatible with gastric emptying time.

For the purpose of defining immediate release forms, the US Food and Drug Administration describes the physical characteristics which must be met in an in vitro release model (Dissolution Testing of Immediate Release Solid Dosage Forms).

Also, sodium oxybate is classified in Class 1 of the Biopharmaceutics Classification System (BCS) i.e. highly soluble and permeable products, in this case more particularly under the aforementioned pH conditions.

To include a safety margin, the FDA Guide logically recommends a standard of more than 85% of active substance released into a medium at pH 1 (0.1N HCl), the pH of the stomach under «fasting» conditions, within 15 minutes to pay heed to the constraints of gastric emptying.

Regarding the granules mentioned above as example, these comprise:
- the active ingredient (GHB or one of the therapeutically acceptable salts thereof);
- an effervescent agent, such as sodium bicarbonate;
- a diluent such as magnesium aluminosilicate e.g. the product marketed under the trade name Neusilin®;
- a binder such as povidone;
- a substrate such as that formed by sugar spheres (sucrose mixed with starch);
- a coating agent e.g. comprising hypromellose, stearic acid and talc, optionally a flavouring agent and a sweetening agent;

The different ingredients other than the active ingredient, namely the effervescent agent, diluent, binder, substrate, coating agent, flavouring agent and sweetening agent are selected from among those cited in international application WO 2012/107652 in the name of the applicant; similarly, the method for obtaining said granules may be the method described in said international application.

Advantageously, these granules have the following composition (weight % relative to the total weight of the granule):
- Active ingredient (sodium oxybate): 50 to 60%;
- Effervescent agent: 5 to 15%;
- Diluent: 2 to 18%;
- Binder: 3 to 10%;
- Substrate (Solid core of the granule): 15 to 25%;
- Coating agent/flavouring agent/sweetening agent/lubricant: 3 to 6%.

More specifically these granules have the following composition (weight % relative to the total weight of the granule):
- Sodium oxybate: 56.02%;
- Sodium bicarbonate: 8.40%;
- Magnesium aluminosilicate: 5.04%;
- Povidone: 5.60%;
- Sugar spheres: 19.66% (in a proportion of 62.5% to 91.5% sucrose per 8.5% to 37.5% starch);
- Coating agent: 0.95% hypromellose, 0.10% stearic acid, 0.05% flavouring agent, 0.83% sucralose (sweetening agent) and 3.34% talc.

Advantageously, these granules are packaged in sachets, sticks in particular, allowing facilitation for the practitioner and for the patient, avoiding any risk of error of dosage for example, whilst allowing easier, safer storage and transport.

Other than the «granule» form just described, other pharmaceutical forms (solid, semi-solid, semi-liquid or liquid), also via oral route and with immediate release, can be envisaged without departing from the scope of the present invention, provided that these forms have a similar pharmacokinetic profile to that of said granules.

If such profile is lacking, the applicant has observed a drop in the bioavailability of the active substance, incompatible with maintained efficacy.

The following tables compare the in vitro and in vivo behaviours of an immediate release form (SMO.IR) and non-immediate release form (SMO.SR). This was a cross over trial conducted in 12 healthy volunteers.

For a pharmaceutical form of sodium oxybate to be considered bioequivalent in accordance with the EMA Guide on Bioequivalence Studies, and is able to meet the characteristics of efficacy, the critical pharmacokinetic parameters (CMax and AUC) must lie within a range of 80 to 125% of those of the reference product. When the TMax value is critical, which is the case for fast-acting immediate release forms, these values must not exhibit a statistically significant difference.

| PK parameters (Mean +/− Standard Deviation) | SMO.IR 1.75 g dose of sodium oxybate | SMO.SR 1.75 g dose of sodium oxybate |
| --- | --- | --- |
| CMax (µg/mL) | 54.5 +/− 15.7 | 31.3 +/− 20.7 |
| TMax (h) | 0.50 | 1.25 |
| AUC t (µg/mL * h) | 70 +/− 46 | 52 +/− 39 |
| T½ (h) | 0.56 +/− 0.26 | 0.56 +/− 0.26 |
| MRT | 1.20 +/− 0.47 | 1.78 +/− 0.45 |

T ½: elimination half-life representing the time to eliminate 50% of absorbed molecules.

To evaluate the exposure of patients to two formulations of one same active substance, it is preferable to compare the MRT (Mean Residence Time) which represents the mean residence time in the body of one molecule of sodium oxybate, and which in this case takes absorption kinetics into account.

Despite logically equivalent elimination values T½, the MRT of the SR form is significantly increased and is due to slower absorption.

The most important parameter in the present invention (development of a solid form with immediate release) is TMax. The TMax of the immediate release form (30 minutes) is coherent with the mean gastric emptying times and allows optimum AUC and CMax values to be obtained (no loss of product) and hence controlled patient exposure. A form that does not have immediate release (SMO.SR) would cause a fall in exposure (significantly reduced AUC and CMax) and loss of efficacy.

The applicant has found the following AUC and CMax values, which are dependent on the doses used, for doses of 0.37 g, 0.75 g, 1.25 g and 1.75 g:

|  | 0.37 g | | 0.75 g | | 1.25 g | | 1.75 g | |
| --- | --- | --- | --- | --- | --- | --- | --- | --- |
|  | Mean | Standard Deviation | Mean | Standard deviation | Mean | Standard deviation | Mean | Standard deviation |
| CMax (µg/mL) | 11.5 | 3.3 | 23 | 6.7 | 39 | 11.2 | 54.5 | 15.7 |
| AUCt (µg/mL*h) | 14.8 | 9.7 | 30 | 19.7 | 50 | 32.9 | 70 | 46 |

To meet the characteristics of the invention, the pharmaceutical form must ideally have a TMax of about 30 minutes and in all cases no longer than 40 minutes (twice the maximum gastric emptying half-life when fasting, i.e. 20 minutes).

Figure 2:
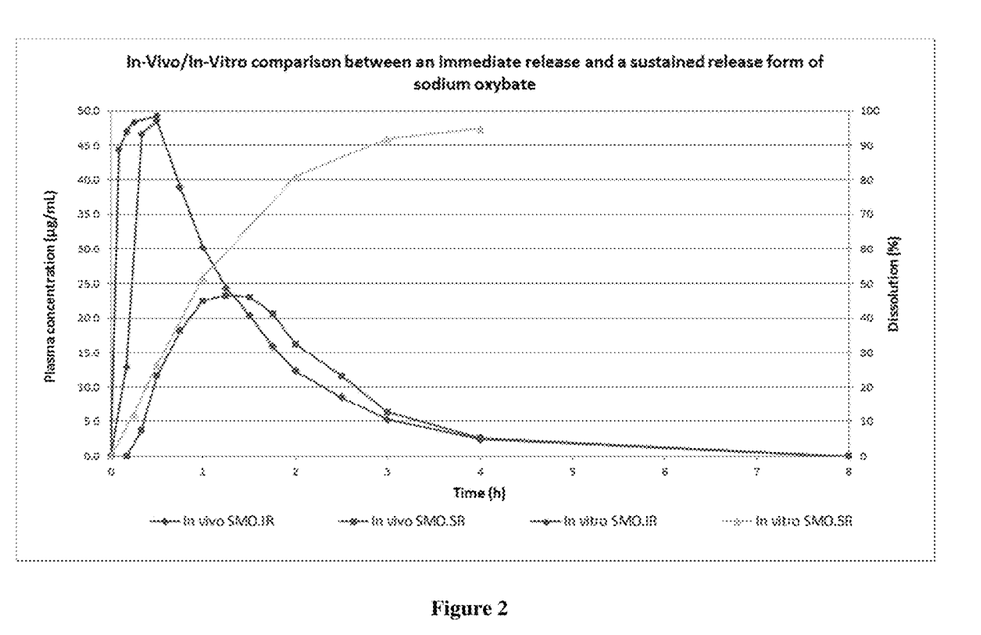

FIG. 2 illustrates the in vivo-in vitro comparison of an immediate release form and a non-immediate release form of sodium oxybate; it follows from this Figure that the in vitro release kinetics and in vivo absorption kinetics exhibit the same slope. The in vitro dissolution model is therefore predictive of the PK behaviour of the formulations.

Within this context, the pharmaceutical forms must ideally exhibit in vitro release of the active ingredient of more than 90% in 15 minutes and in any case higher than 85% to meet the definitions of immediate release forms in force (FDA Guides on the development of immediate release forms).

Analysis of the data from the aforementioned phase IIb/III trial showed a statistically very significant interaction ($p=0.0012$) between the efficacy of treatment, the daily level of alcohol intake and the unit dose of sodium oxybate taken three times daily.

For the two categories of patients analysed (cf. categories described above), PDA linear and quadratic models showed statistically significant relationships between the level of efficacy and the dose of sodium oxybate given to the patients.

Patients with severe or very severe alcohol dependence

Figure 3:
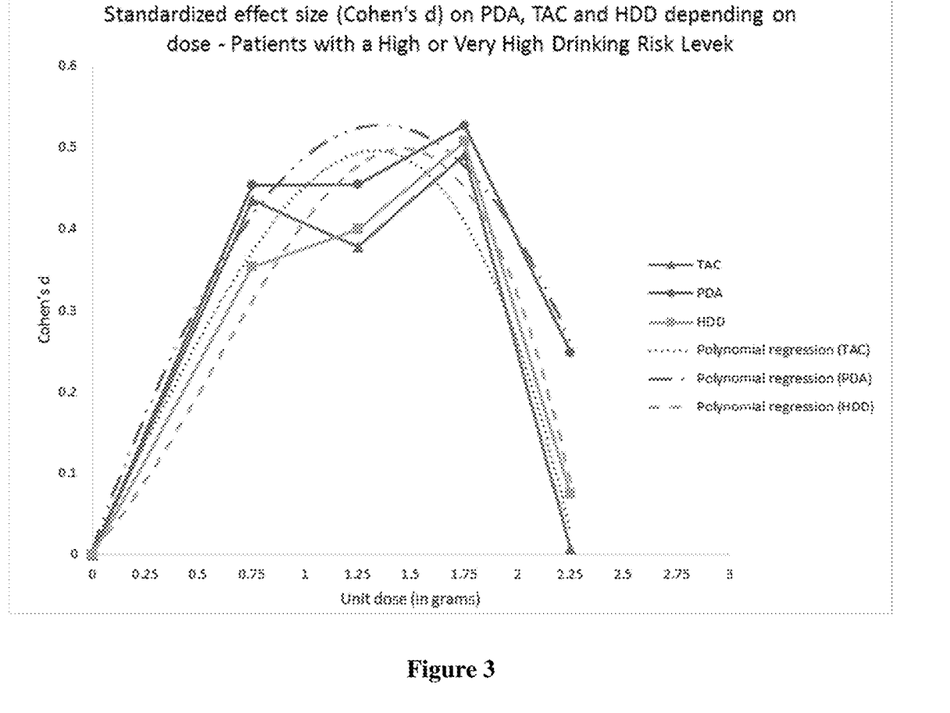

In severely or very severely alcohol-dependent patients without liver disease, these statistical models showed that the efficacy of sodium oxybate in maintaining abstinence increased progressively when the unit doses administered three times daily were increased, a statistically significant result being reached with the dose of 1.75 g ($p<0.05$). This is illustrated in FIG. 3. The polynomial regression models also showed that the optimum in patients with severe or very severe alcohol dependence, without liver disease, is reached with a dose of about 1.5 g. Over and above doses of 1.75 g or below 1.25 g, efficacy is substantially decreased.

Therefore, the doses between 1.25 g and 1.75 g sodium oxybate three times daily have the highest efficacy results. The dose of 1.50 g three times daily can be considered to be the optimal dose.

It is important to point out that the doses lower than 1.25 g or higher than 1.75 g showed efficacy results up to 80% lower than the optimal dose.

Patients with mild or moderate alcohol dependence

In mildly or moderately alcohol-dependent patients without liver disease, the statistical models showed that optimum efficacy was reached with a dose of 0.75 g three times daily, followed by a decrease in efficacy with doses above 1.25 g sodium oxybate three times daily.

Therefore, in patients with mild or moderate alcohol dependence, the unit doses between 0.75 g and 1.25 g sodium oxybate three times daily have the highest efficacy results, and the unit dose of 0.75 g three times daily represents the optimal dose.

The doses higher than 1.25 g showed a drop in efficacy, possibly down to about 20% of the efficacy of the optimal dose.

Dose-Response relationship

As previously mentioned, the unit dose of the invention is determined as a function of the patient's drinking level.

Figure 4:
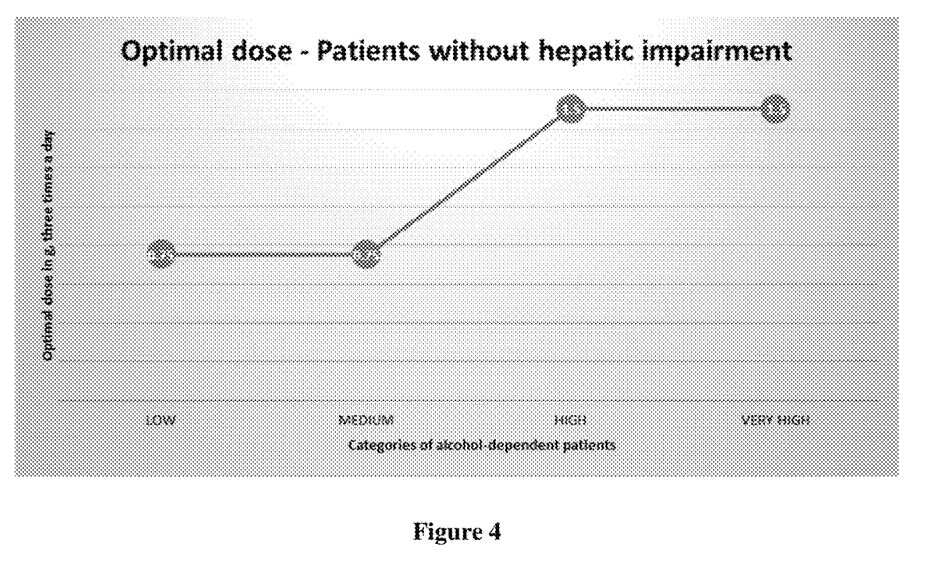

FIG. 4 illustrates the dose-response identified as a function of alcohol intake before weaning in patients without liver disease.

For patients with mild or moderate alcohol-dependence without liver disease, the dose of 0.75 g three times daily appears to be the optimal dose.

For patients with severe or very severe alcohol dependence without liver disease, the dose of 1.50 g three times daily appears to be the optimal dose.

Figure 5:
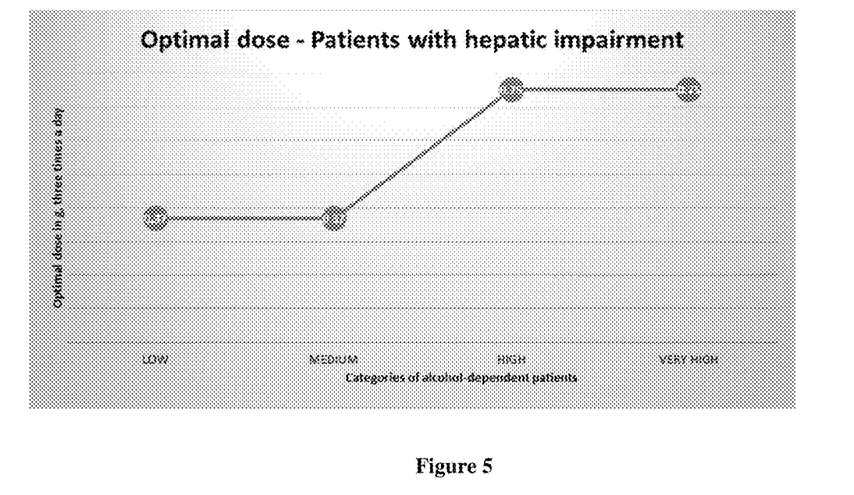

As indicated previously, the doses must be divided in half for patients suffering from liver disease. Therefore, for these patients, the dose ranges for patients with mild or moderate alcohol dependence lie between 0.37 and 0.62 g in three daily doses, and between 0.62 and 0.87 g in three daily doses for patients that are severely or very severely alcohol-dependent. The optimal doses within these ranges i.e. 0.37 g for patients with mild or moderate alcohol dependence, and 0.75 g for patients with severe or very severe alcohol dependence are illustrated in FIG. 5.

As mentioned previously, the applicant went against the state of the art which systematically recommends a dosage taking patient weight into account.

In addition, it has been demonstrated that an inaccurate dosage compared with the optimal dosage defined by the applicant could lead to a significant loss of efficacy with an increase in the side effects related to sodium oxybate.

Figure 6:
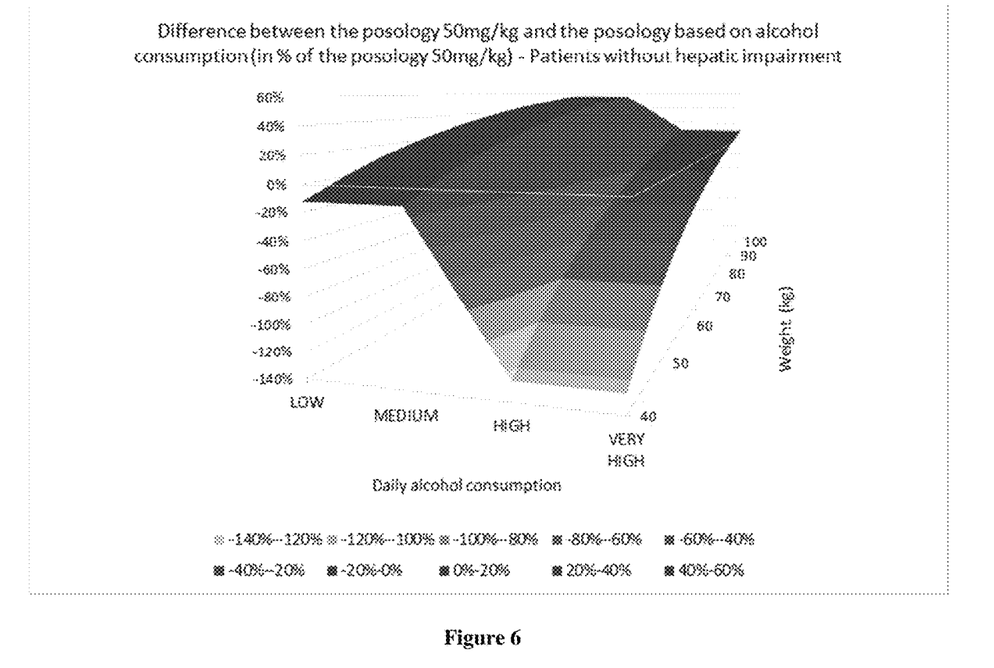

Also, the applicant has illustrated in the Figures below that these situations of non-optimal dosage delivery may be very frequent in patients without liver disease (FIGS. 6 and 7) or with liver disease (FIGS. 8 and 9):

Patients without Liver Disease:

FIG. 6 represents the difference (%) between dosage based on the state of the art (50 mg/kg/day) and the dosage discovered by the applicant for patients without liver disease. This Figure indicates that for a patient with mild or moderate alcohol dependence weighing 75 kg without liver disease, the lower limit of the dosage such as defined in the state of the art (50 mg/kg/day) would have led to an over-dosage in the order of 40% relative to the optimal dosage discovered and determined by the applicant. In contrast, for patients with severe or very severe alcohol dependence, without liver disease, the dosage such as defined by the state of the art of 50 mg/kg/day would amount to an under-dosage possibly reaching up to −125% as a function of patient weight in relation to the optimal dosage defined by the applicant.

Figure 7:
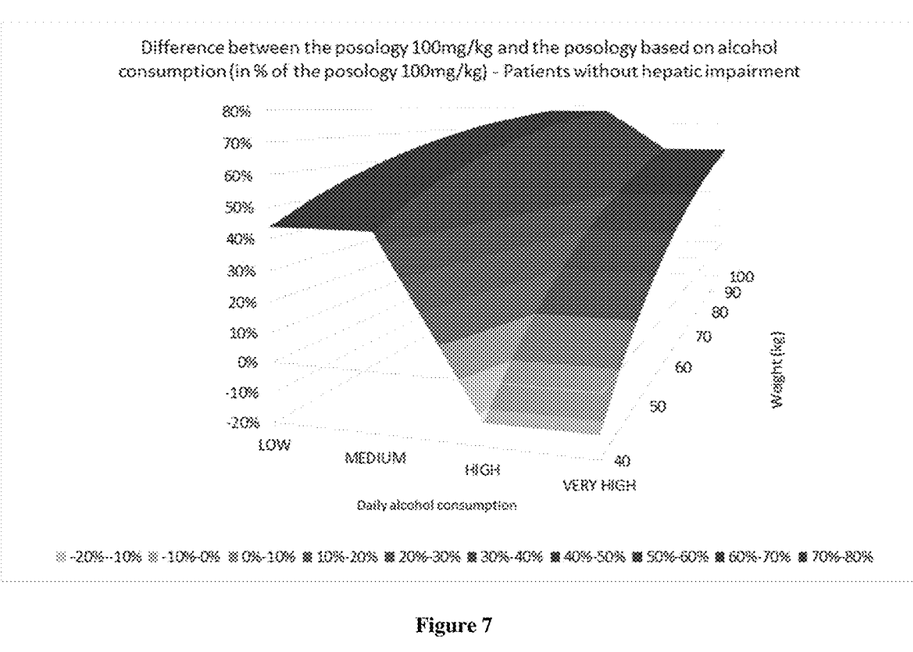

FIG. 7 shows the differences (expressed as %) between the upper limit of the dosage in the prior art (100 mg/kg/day) and the dosage discovered by the applicant. This Figure shows that for a patient with mild or moderate alcohol dependence, without liver disease, the upper limit of dosage such as defined in the state of the art (100 mg/kg/day) would have led to an over-dosage in the order of 44% to 80% in relation to the optimal dosage discovered and determined by the applicant. In contrast, and for patients with severe or very severe alcohol dependence without liver disease, the dosage such as defined in the state of the art of 100 mg/kg/day would amount to an over-dosage of between 10% and 55% for patients weighing more than 50 kg in relation to the optimal dosage defined by the applicant.

Figure 8:
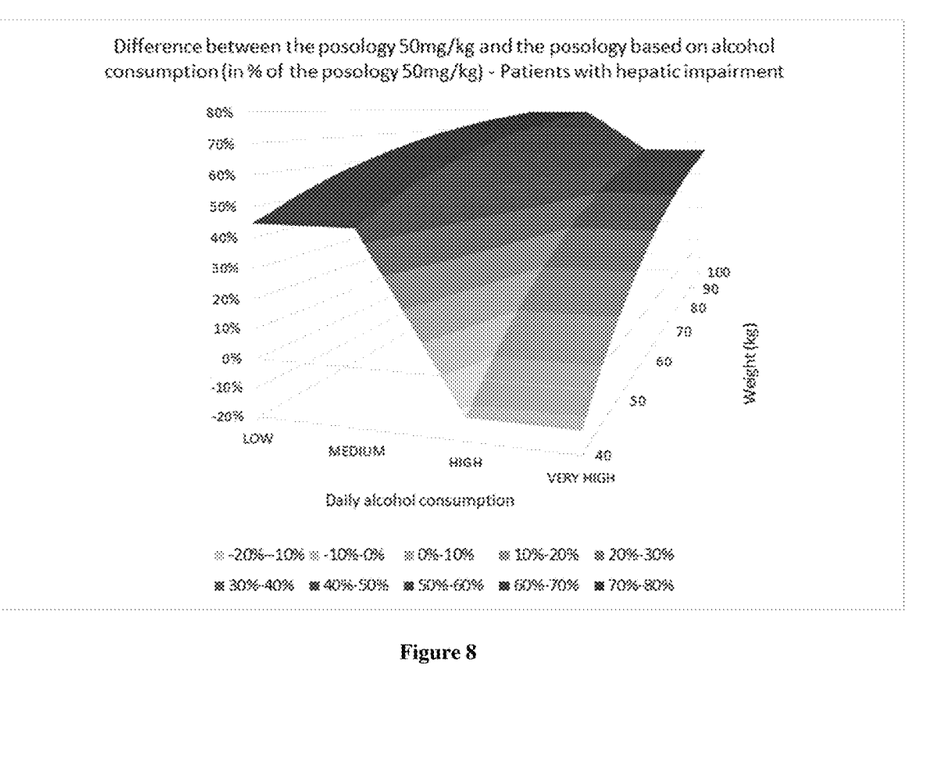

Patients with Liver Disease:

FIG. 8 shows the difference (%) between the dosage based on the state of the art (50 mg/kg/day) and the dosage discovered by the applicant for patients with liver disease. This Figure indicates that for a patient with mild or moderate alcohol dependence suffering from liver disease, the lower limit of dosage such as defined in the state of the art (50 mg/kg/day) would have led to an over-dosage in the order of 45% to 80% relative to the optimal dosage discovered and determined by the applicant. In contrast, for patients with severe or very severe alcohol dependence and suffering from liver disease, the dosage such as defined by the state of the art of 50 mg/kg/day would amount to an over-dosage of between 10% and 55% for patients weighing more 50 kg in relation to the optimal dosage defined by the applicant.

Figure 9:
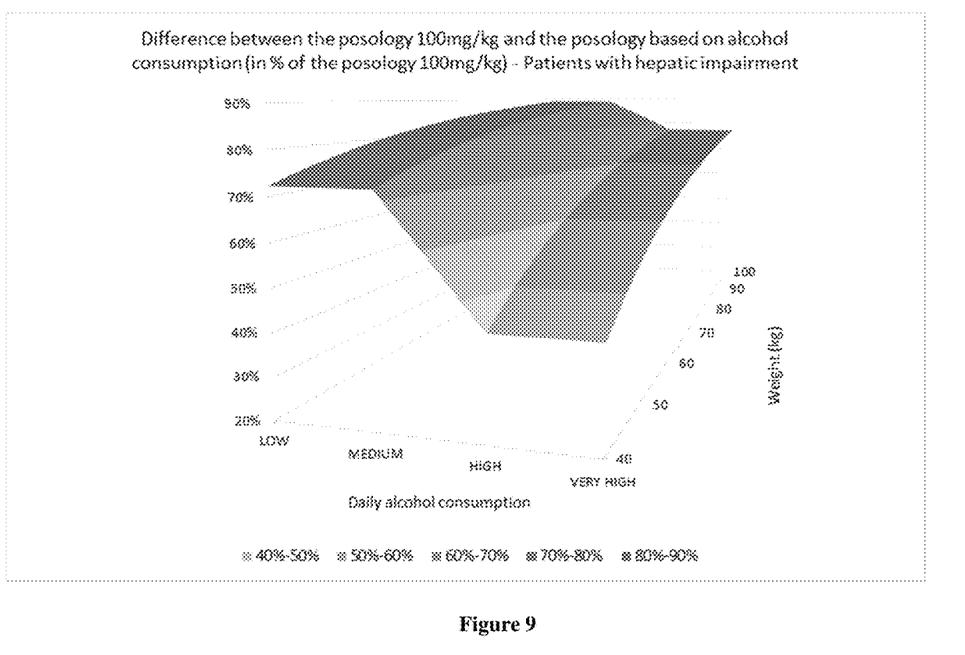

FIG. 9 shows the differences (expressed as %) between the upper limit of the dosage in the state of the art (100 mg/kg/day) and the dosage discovered by the applicant for a patient with liver disease. This Figure indicates that for patients with mild or moderate alcohol dependence suffering from liver disease, the upper limit of the dosage such as defined in the state of the art (100 mg/kg/day) would have led to an over-dosage in the order of 72% to 89% in relation to the optimal dosage discovered and determined by the applicant. For patients with severe or very severe alcohol dependence suffering from liver disease, the dosage such as defined in the state of the art of 100 mg/kg/day would amount to an over-dosage of between 44% and 78% relative to the optimal dosage defined by the applicant.

It follows from the foregoing that the unit doses of the invention vary from 0.37 g to 1.75 g in three daily doses, and narrower ranges and optimal doses have been determined taking into account both the level of patient alcoholism (mild or moderate on one hand, or severe or very severe on the other hand) and the fact that this patient does or does not suffer from liver disease.

To summarise, the applicant has been able to determine that for patients with mild or moderate alcohol dependence and not suffering from liver disease, a unit dose of 0.75 to 1.25 g, three times daily gives excellent results. Below 0.75 g the results did not appear to be sufficiently conclusive. In addition, doses higher than 1.25 g three times daily showed significantly lesser efficacy in patients with mild or moderate alcohol dependence. The best results were obtained with a unit dose of 0.75 g, taken three times daily.

For patients with mild or moderate alcohol dependence and suffering from liver disease, a range of unit doses of 0.37 to 0.62 g taken three times daily gave satisfactory results, on the understanding that the dose of 0.37 g three times daily appears to be the optimal dose.

In respect of patients with severe or very severe alcohol dependence and not suffering from liver disease, the applicant was able to demonstrate that a unit dose of 1.25 to 1.75 g taken three times daily gave the best results; below 1.25 g the dose is not sufficient for patients that are severely or very severely alcohol dependent, and it is rather more indicated as just mentioned for patients with mild or moderate alcohol dependence. Above 1.75 g, efficacy decreases significantly and the side effects become more numerous and frequent, in particular a sedative effect with nausea and marked fatigue for the patient; the applicant was able to demonstrate that the optimal dose for patients with severe or very severe alcohol dependence without liver disease is 1.50 g taken three times daily.

For patients with this level of alcohol consumption and suffering from liver disease, the recommended doses range from 0.62 to 0.87 g taken three times daily, the optimal dose being 0.75 g three times daily.

Finally, it is only exceptionally that a patient in whom the conventional method is used (dosage determined as a function of weight) would be delivered the suitable dose such as recommended by the applicant.

In this respect, the applicant has been able to demonstrate that the conventional method could generate major under-dosages or over-dosages possibly reaching up to more than 10 times the optimal dose determined by the applicant.

The invention claimed is:

1. A method of maintaining alcohol abstinence in a patient, comprising
    determining a dosage of GHB or a therapeutically acceptable salt thereof as an active ingredient for a patient in need of alcohol abstinence, based on daily alcohol consumption of the patient and independent of a weight of the patient, and
    administering the determined dosage of the GHB or a therapeutically acceptable salt thereof to the patient,
    wherein the dosage comprises three unit doses of the GHB or a therapeutically acceptable salt thereof administered daily, each of the unit doses of the dosage comprising between 0.37 and 1.75 g of the active ingredient, and the active ingredient has an in vitro release higher than 85% in fifteen minutes.

2. The method according to claim 1, wherein each of the unit doses comprises between 0.75 and 1.25 g of the active ingredient for administration to a patient having mild or moderate risk levels for alcohol dependence, as defined by the World Health Organization in WHO/MSD/MSB/00.4, without liver disease.

3. The method according to claim 2, wherein each of the unit doses contains 0.75 g of the active ingredient.

4. The method according to claim 1, wherein each of the unit doses comprises between 0.37 and 0.62 g of the active ingredient for administration to a patient having mild or moderate risk levels for alcohol dependence, as defined by the World Health Organization in WHO/MSD/MSB/00.4, with liver disease.

5. The method according to claim 4, wherein each of the unit doses contains 0.37 g of the active ingredient.

6. The method according to claim 1, wherein each of the unit doses comprises between 1.25 and 1.75 g of the active ingredient for administration to a patient having severe or very severe risk levels for alcohol dependence, as defined by the World Health Organization in WHO/MSD/MSB/00.4, without liver disease.

7. The method according to claim 6, wherein each of the unit doses contains 1.50 g of the active ingredient.

8. The method according to claim 1, wherein each of the unit doses comprises between 0.62 and 0.87 g of the active ingredient for administration to a patient having severe or very severe risk levels for alcohol dependence, as defined by the World Health Organization in WHO/MSD/MSB/00.4, with liver disease.

9. The method according to claim 8, wherein each of the unit doses contains 0.75 g of the active ingredient.

10. The method according to claim 1, wherein the active ingredient has an in vitro release higher than 90% in fifteen minutes.

11. The method according to claim 1, wherein the three unit doses are administered orally.

\* \* \* \* \*